United States Patent
Stamm et al.

(10) Patent No.: US 6,337,425 B1
(45) Date of Patent: Jan. 8, 2002

(54) METHOD FOR CHLORINATING KETONES

(75) Inventors: Armin Stamm, Mainz; Jochem Henkelmann, Mannheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/646,186

(22) PCT Filed: Mar. 10, 1999

(86) PCT No.: PCT/EP99/01712

§ 371 Date: Sep. 14, 2000

§ 102(e) Date: Sep. 14, 2000

(87) PCT Pub. No.: WO99/47479

PCT Pub. Date: Sep. 23, 1999

(30) Foreign Application Priority Data

Mar. 19, 1998 (DE) .......................................... 198 12 095

(51) Int. Cl.[7] .............................................. C07C 17/02
(52) U.S. Cl. ...................................................... 570/217
(58) Field of Search .......................................... 570/217

(56) References Cited

U.S. PATENT DOCUMENTS

| 3,715,407 A | 2/1973 | Relles |
| 4,044,060 A | 8/1977 | Buysch et al. |

FOREIGN PATENT DOCUMENTS

| DE | 25 25 442 | 12/1976 |
| DE | 197 09 401 | 9/1998 |

OTHER PUBLICATIONS

Horner et al. "Annalem der Chemie" Liebigs Ann. 626 (1959) pp. 28, 29, 32 and 33.

Primary Examiner—Alan Siegel
(74) Attorney, Agent, or Firm—Keil & Weinkauf

(57) ABSTRACT

In a process for chlorinating ketones which, apart from the carbonyl group, are inert in respect of triarylphosphine dichlorides, except for cyclopropyl methyl ketone, in which the ketones are reacted with a chlorinating agent in the presence of triarylphosphine oxides, the amount of triarylphosphine oxide is from 0.1 to 10 mol %, based on the amount of ketone. The ketones preferably have a least one CH-acid proton in the $\alpha$ position to the carbonyl group.

8 Claims, No Drawings

METHOD FOR CHLORINATING KETONES

The present invention relates to a process for chlorinating ketones, in particular ketones which have at least one CH-acid proton in the α position to the carbonyl group. Chlorination of these ketones forms predominantly chlorine-substituted alkenes.

Chlorinated alkenes are valuable intermediates for organic synthesis, since they can easily be functionalized further. Thus, for example, substituted alkynes are obtainable by elimination using bases.

Chlorinated alkenes can, for example, be prepared from ketones using suitable chlorinating agents. A particularly suitable chlorinating agent is $PCl_5$, phosphorus pentachloride. By means of phosphorus pentachloride, ketones can almost universally be converted into the corresponding chloroalkenes. However, as a starting material on an industrial scale, phosphorus pentachloride can only be handled with considerable difficulty since it is a very hygroscopic, corrosive solid which gives off hydrochloric acid fumes on contact with moisture. In addition, chlorination using phosphorus pentachloride is uneconomical since only 2 of the 5 chlorine atoms are usable and it is an expensive starting material.

Alternative reagents such as oxalyl chloride or triphenylphosphine in carbon tetrachloride are frequently usable only on a laboratory scale. The reaction of ketones in the presence of formamides as solvents leads to formulation of the double bond at the same time as chlorination.

The chlorination of ketones and aldehydes using triphenylphosphine dichloride is also known. Liebigs Ann. 626 (1959), pages 28, 29, 32 and 33 describe the synthesis of geminal dihalides from aldehydes and ketones by reaction with triphenylphosphine dichloride. In the case of ketones having acidic protons in the α position, chlorinated alkenes are obtained. The triphenylphosphine dichloride is used in the reaction in equimolar amounts, based on the ketone.

The process has the disadvantage that the reaction has to be carried out in a suspension because of the sparing solubility of the triphenylphosphine dichloride. On an industrial scale, this is often associated with stirring difficulties. In addition, triphenylphosphine dichloride is highly corrosive and very hygroscopic, which makes handling this compound difficult. Triphenylphosphine oxide is formed as waste product and has to be disposed of.

U.S. Pat. No. 3,715,407 describes a process for chlorinating ketones using triphenylphosphine oxide. Here, triphenylphosphine oxide is reacted with phosgene to form triphenylphosphine dichloride which then reacts with the keto group. This liberates carbon dioxide from the phosgene, as a result of which the reaction is driven in the direction of the products. According to U.S. Pat. No. 3,715,407, the triphenylphosphine oxide is used in excess, preferably in a two-fold or greater excess, based on the ketone. The use of these large amounts of triphenylphosphine oxide makes the use of a suitable solvent necessary. In addition, the reaction again forms a large amount of phosphorus-containing wastes which have to be disposed of.

DE-A-197 09 401, which has earlier priority but is not a prior publication, discloses a process for halogenating cyclopropyl methyl ketone in which cyclopropyl methyl ketone is reacted with triphenylphosphine dichloride which is prepared in situ by reaction of triphenylphosphine oxide with phosgene. Here, the use of catalytic amounts of triphenylphosphine oxide is sufficient to enable the process to be carried out successfully.

It is an object of the present invention to provide a process for chlorinating ketones which avoids the disadvantages of the known processes and can be applied to many different ketones.

We have found that this object is achieved by a process for chlorinating ketones which, apart from the carbonyl group, are inert in respect of triarylphosphine dichlorides, except for cyclopropyl methyl ketone, in which the ketones are reacted with a chlorinating agent in the presence of triarylphosphine oxides, wherein the amount of triarylphosphine oxide is from 0.1 to 10 mol %, based on the amount of ketone.

In the process of the present invention, a triarylphosphine oxide, preferably triphenylphosphine oxide, is added to the reaction mixture in catalytic amounts of from 0.1 to 10 mol %, preferably from 0.5 to 5 mol %, particularly preferably from 1 to 3 mol %, based on the amount of ketone. Passing phosgene continuously into the reaction mixture then converts the triphenylphosphine oxide into triphenylphosphine dichloride, the actual reactive species, with parallel formation of carbon dioxide.

According to the present invention, it has been found that the use of only catalytic amounts of triarylphosphine oxide is sufficient to achieve complete chlorination of many ketones. The use of catalytic amounts of triphenylphosphine oxide eliminates the need to use a solvent for the reaction. According to the present invention, the chlorination is preferably carried out without solvents, which results in a considerable increase in the space-time yield. The triarylphosphine oxide can be dissolved in the ketone which is preferably converted into the alkenyl chloride by chlorination, as long as the ketone is liquid at the reaction temperature, preferably also at room temperature. In small amounts as are used according to the present invention, the triarylphosphine oxide is completely soluble in the ketone, as a result of which deposits on parts of the plant or valve blockages are avoided. Another advantage is the significantly reduced amount of phosphorus-containing reaction residue.

If the ketone is one which is solid at the reaction temperature, it is possible to make use of solvents which are inert toward phosgene, for example aromatic or aliphatic hydrocarbons such as toluene, xylene or chlorobenzene or else carboxylic esters such as ethyl acetate or cyclic ethers such as dioxane or tetrahydrofuran.

The reaction temperature is preferably in the range from 70 to 200° C., particularly preferably in the range from 80 to 150° C. The process can be carried out batchwise or preferably continuously. The reaction products can be distilled from the reaction mixture or reactor output and subsequently be further purified if necessary. The catalyst present in the distillation residue is preferably returned to the reaction or can be disposed of. The entire distillation residue can, according to the present invention, be returned to the reaction.

According to the present invention, any suitable chlorinating agents can be used. Examples of suitable chlorinating agents are phosgene, thionyl chloride, oxalyl chloride, diphosgene and triphosgene. Preference is given to using phosgene since it is a very inexpensive and readily available chlorinating agent which in the reaction forms only gaseous by-products which are simple to remove from the reaction mixture.

In the chlorination according to the present invention, it is possible to use all ketones which, apart from the carbonyl group, are inert in respect of triarylphosphine dichloride. Here, the use of cyclopropyl methyl ketone as described in DE-A-197 09 401, which has earlier priority but is not a prior publication, is excluded from the scope of the present invention. The ketone can thus have any structure as long as only the carbonyl group reacts with triarylphosphine chloride under the reaction conditions. The ketone should, for example, have no hydroxyl groups which react with the triarylphosphine dichloride under the reaction conditions.

The ketones used according to the present invention preferably have at least one CH-acid proton in the a position to the carbonyl group. The CH-acid proton is preferably present in the form of a methylene or methine group. The ketone is preferably selected from among ketones of the formula I

R—C(O)—CH$_2$—R'  (I)

where R and R' are, independently of one another, $C_1$–$C_{20}$-alkyl, which may be unbranched, branched or at least partly closed to form a cyclic system and may be interrupted by from 1 to 5 oxygen atoms, or $C_6$–$C_{18}$-aryl, where the alkyl radicals may be substituted by $C_6$–$C_{18}$-aryl, halogen or nitro and the aryl radicals may be substituted by $C_1$–$C_{20}$-alkyl, halogen or nitro, or R and R' together form a $C_1$–$C_{20}$-alkylene group which may be substituted by $C_1$–$C_{20}$-alkyl, $C_6$–$C_{18}$-aryl, halogen or nitro and may be interrupted by from 1 to 5 oxygen atoms, where 2 carbon atoms in the ring may be part of a further cyclic aliphatic or aromatic system, with the exception of cyclopropyl methyl ketone.

The reaction of the ketones of the formula I generally gives a mixture of the geminal dichloro compound R—C(Cl$_2$)—CH$_2$R' and the stereoisomer chloroalkenyl compound of the formula R—C(Cl)=CH—R'.

The reaction generally leads predominantly to the chloroalkenyl compounds (chlorine-substituted alkenes). In the case of, for example, carbonyl compounds having two aromatic substituents, e.g. benzophenone, only the geminal dichloro compounds are formed in the chlorination.

The ketones used according to the present invention preferably have no halogen or nitro substituents and are not interrupted by oxygen atoms. They are therefore preferably ketones which are, apart from the carbonyl group, built up entirely of carbon and hydrogen. Particularly preferably, R and R' are, independently of one another, $C_1$–$C_{10}$-alkyl or $C_6$–$C_{12}$-aryl or together $C_1$–$C_5$-alkylene. In particular, R and R' are, independently of one another, $C_1$–$C_6$-alkyl or phenyl or together $C_2$–$C_4$-alkylene. Examples of particularly preferred ketones are acetophenone, propiophenone, cyclohexanone, cyclopentanone, propanone and dibutanone isomers, pentanone isomers, hexanone isomers, heptanone isomers and octanone isomers. In particular, cyclopentanone or cyclohexanone is used in the reaction.

The invention is illustrated by the examples below.

EXAMPLES

Example 1

The experiments were carried out in a standard 500 ml stirred apparatus fitted with gas inlet and a carbon dioxide condenser. 5.6 g of triphenylphosphine oxide (0.02 mol) are dissolved in 78.4 g (0.8 mol) of cyclohexanone. At from 100 to 120° C., a total of 82 g (0.82 mol) of gaseous phosgene are passed in over a period of 6 hours. After stripping out the excess phosgene by means of nitrogen, the product (84.4 g) is fractionally distilled. 43.1 g (0.37 mol) of 1-chlorocyclohexene (content according to GC: >99% by area) go over at 35–37° C. at 17 mbar.

Example 2

5.6 g of triphenylphosphine oxide (0.02 mol) are dissolved in 91.4 g (0.8 mol) of 2-heptanone. At from 100 to 125° C., a total of 95 g of phosgene (0.95 mol %) are passed in over a period of 7 hours. Stripping out the excess phosgene by means of nitrogen leaves 107.1 g of product. Fractional distillation under reduced pressure (42 mbar, 53–70° C.) gives 85 g of a mixture of the three isomeric chloroheptenes (cis- and trans-2-chloro-2-heptene and 2-chloro-1-heptene) and 2,2-dichloroheptane.

Example 3

5.6 g of triphenylphosphine oxide (0.02 mol) are dissolved in 96 g (0.8 mol) of acetophenone. At from 80 to 120° C., a total of 90 g (0.9 mol) of gaseous phosgene are passed in over a period of 9 hours. Stripping out the excess phosgene by means of nitrogen leaves 110.6 g of product. According to GC, this still contains 6% of the starting material together with 79% (87 g) of 1-phenylvinyl chloride and 2% (2.2 g) of 1,1-dichlorophenylethane. Fractional distillation (0.3 mbar, 36° C.) gives 77.5 g of colorless liquid having a 1-phenylvinyl chloride content of >90%.

We claim:

1. A process for preparing alkenyl chlorides by chlorinating ketones which have at least one CH-acid proton in the α position to the carbonyl group and which, apart from the carbonyl group, are inert in respect of triarylphosphine dichlorides, except for cyclopropyl methyl ketone, in which the ketones are reacted with a chlorinating agent in the presence of triarylphosphine oxide, the amount of triarylphosphine oxide being from 0.1 to 10 mol %, based on the amount of ketone.

2. A process as claimed in claim 1, wherein the ketones are selected from among ketones of the formula I

R—C(O)—CH$_2$—R'  (I)

where R and R' are, independently of one another, $C_1$–$C_{20}$-alkyl, which may be unbranched, branched or at least partly closed to form a cyclic system and may be interrupted by from 1 to 5 oxygen atoms, or $C_6$–$C_{18}$-aryl, where the alkyl radicals may be substituted by $C_6$–$C_{18}$-aryl, halogen or nitro and the aryl radicals may be substituted by $C_1$–$C_{20}$-alkyl, halogen or nitro, or R and R' together form a $C_1$–$C_{20}$-alkylene group which may be substituted by $C_1$–$C_{20}$-alkyl, $C_6$–$C_{18}$-aryl, halogen or nitro and may be interrupted by from 1 to 5 oxygen atoms, where 2 carbon atoms in the ring may be part of a further cyclic aliphatic or aromatic system, and are chlorinated to chloroalkenyl compounds of the formula R—C(Cl)=CH—R'.

3. A process as claimed in claim 2, wherein R and R' are, independently of one another, $C_1$–$C_{10}$-alkyl or $C_6$–$C_{12}$-aryl or together $C_1$–$C_5$-alkylene.

4. A process as claimed in claim 1, wherein the chlorinating agent used is phosgene.

5. A process as claimed in claim 1, wherein the triarylphosphine oxide used is triphenylphosphine oxide.

6. A process as claimed in claim 1, wherein the chlorination is carried out in the absence of solvent.

7. A process as claimed in claim 2, wherein the chlorination products obtained are predominantly chlorine-substituted alkenes.

8. A process as claimed in claim 1, wherein the reaction products are removed from the reaction mixture by distillation and catalyst present in the residue is returned to the reaction.

* * * * *

UNITED STATES PATENT AND TRADEMARK OFFICE
CERTIFICATE OF CORRECTION

PATENT NO.    : 6,337,425 B1
DATED         : January 8, 2002
INVENTOR(S)   : Stamm et al.

It is certified that error appears in the above-identified patent and that said Letters Patent is hereby corrected as shown below:

<u>Column 4,</u>
Line 22, after "proton" insert -- present in the form of a methylene or methine group --.

Signed and Sealed this

Thirteenth Day of August, 2002

*Attest:*

*Attesting Officer*

JAMES E. ROGAN
*Director of the United States Patent and Trademark Office*